(12) United States Patent
Milo

(10) Patent No.: US 6,183,432 B1
(45) Date of Patent: *Feb. 6, 2001

(54) GUIDEWIRE AND CATHETER WITH ROTATING AND RECIPROCATING SYMMETRICAL OR ASYMMETRICAL DISTAL TIP

(75) Inventor: Charles F. Milo, Union City, CA (US)

(73) Assignee: Lumend, Inc., Redwood City, CA (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/969,814

(22) Filed: Nov. 13, 1997

(51) Int. Cl.⁷ .............................. A61B 17/20; A61B 17/22
(52) U.S. Cl. ............................................. 604/22; 606/159
(58) Field of Search .................. 604/20, 22, 96; 606/1, 159, 167, 171, 180, 169, 170, 178; 600/463, 471, 585

(56) References Cited

U.S. PATENT DOCUMENTS

| | | | |
|---|---|---|---|
| 4,749,376 | 6/1988 | Kensey et al. | 604/22 |
| 5,116,350 | 5/1992 | Stevens . | |
| 5,234,451 | 8/1993 | Osypka . | |
| 5,243,997 | 9/1993 | Uflacker et al. . | |
| 5,312,427 | 5/1994 | Shturman | 606/159 |
| 5,397,301 | 3/1995 | Pflueger et al. | 604/22 |
| 5,464,016 | * 11/1995 | Nicholas et al. | 128/662.06 |
| 5,549,119 | 8/1996 | Solar . | |
| 5,584,843 | 12/1996 | Wulfman et al. | 606/159 |
| 5,593,415 | 1/1997 | Adrian . | |
| 5,655,537 | 8/1997 | Crowley | 128/662.06 |
| 5,681,336 | 10/1997 | Clement et al. | 606/159 |

* cited by examiner

*Primary Examiner*—Glenn K. Dawson
*Assistant Examiner*—Michael J. Hayes
(74) *Attorney, Agent, or Firm*—Wilson Sonsini Goodrich & Rosati (57) ABSTRACT

A guidewire or a catheter for crossing vascular occlusions comprises a shaft having a proximal end and a distal end, and a drive member having a proximal and a distal end, the drive member being rotatably disposed within and along a longitudinal axis of the guidewire shaft. An actuator is connected to the proximal end of the drive member, the actuator imparting a rotation to the drive member. An asymmetrical rotating tip is attached to the distal end of the drive member and driven in rotation about the longitudinal axis of the shaft by the drive member. The rotating tip may include a protruding portion that projects from a plane defined by an outer surface of the guidewire shaft to render the rotating tip asymmetrical with respect to the longitudinal axis of the shaft. The protruding portion creates a volume of revolution as the asymmetrical tip rotates, which facilitates crossing a vascular occlusion by displacing and exerting pressure on stenotic material causing the occlusion. Alternatively, the rotating tip may be symmetrical. A coupling member may be attached to the distal end of the shaft and may include a distal angled surface. When the tip includes a mating angled surface, rotation of the drive member causes the tip to undergo both a reciprocal and a rotational motion along and about the longitudinal axis of the shaft.

5 Claims, 5 Drawing Sheets

GUIDEWIRE AND CATHETER WITH ROTATING AND RECIPROCATING SYMMETRICAL OR ASYMMETRICAL DISTAL TIP

BACKGROUND OF THE INVENTION

1. Field of the Invention

The invention relates to guide wires and catheters for crossing, opening and/or widening a channel through a totally or partially occluded biological vessel, such as a blood vessel.

2. Description of the Related Art

There are a number of disease conditions involving stenosis, which is the narrowing or obstruction of the interior passage, or lumen, of arteries. These obstructions, generally known as occlusions, are found in patients suffering from atherosclerosis, a condition characterized by an accumulation of fibrous, fatty or calcified tissue in the arteries. As these occlusions can partially or totally block the arterial flow, they can be potentially life threatening. Occlusions may be partial or total, may be soft and pliable or hard and calcified, and may be found at a great variety of sites in the arterial system, including the aorta, the coronary and carotid arteries, and peripheral arteries.

Although the majority of interventional procedures such as balloon angioplasty, atherectomy, and the like bring some degree of relief to the patient and improvement in the blood flow, total or near total occlusions are difficult to treat, as the interventional tool, such as the angioplasty balloon or the atherectomy catheter, often cannot reach and cross the occlusion site to carry out their intended functions. This is generally referred to as an inability to cross, and is the major cause of failure of such procedures.

A number of different instruments have been proposed to open or to cross a totally or partially blocked blood vessel. One such instrument is disclosed in U.S. Pat. No. 5,116,350 to Stevens. Stevens describes a catheter whose distal blunt tip moves back and forth in a ramming motion or whose cutting/abrading distal tip moves back and forth about an axis. Osypka, in U.S. Pat. No. 5,234,451 discloses an apparatus for eliminating occlusions and stenoses in body cavities. The device of Osypka includes a combination of anvil and reciprocating internal hammer to ram the device through occlusions. The hammer repeatedly strikes the anvil to drive the device further within the cavity. Uflacker et al., in U.S. Pat. No. 5,243,997 propose a device to vibrate a guidewire. The vibration induced thereon is asserted to facilitate the pushing of the guidewire past the obstruction. Solar, in U.S. Pat. No. 5,549,119 discloses a vibrating tip catheter, the vibration being asserted to enhance the catheter's ability to cross tight lesions and stenoses.

These devices, however, suffer from a number of disadvantages. It is believed that the sharp back and forth ramming motions of some of these devices may possibly damage the vessel lining and lead to unwanted scar tissue. On the other hand, the vibrating guide wires and tips are not believed wholly effective in crossing total occlusions without damaging the vessel walls. Moreover, it is not believed that these devices possess the ability to sufficiently enlarge an existing channel to allow other, larger, or more aggressive interventional tools to follow and to position themselves across the occlusion.

What is needed, therefore, are improved guide wires and catheters that are able to successfully navigate tortuous regions of a patient's vasculature and to create or enlarge a channel past an occlusion to allow other interventional tools to successfully perform their intended therapeutic functions. What is also needed are such guide wires and catheters that are effective in opening or enlarging channels past an occlusion, while not damaging the vessel walls.

SUMMARY OF THE INVENTION

It is, therefore, an object of the present invention to provide improved guide wires and catheters that are able to successfully navigate tortuous regions of a patient's vasculature and to create or enlarge a channel to allow other interventional tools to successfully cross the lesion.

It is a further object of the present invention to provide such guide wires and catheters that are effective in opening or enlarging channels past an occlusion, while not damaging the vessel walls.

In accordance with the above objects and those that will be mentioned and will become apparent below, the guidewire for crossing vascular occlusions according to an embodiment of the present invention comprises:

a guidewire shaft having a proximal end and a distal end;
 a drive member having a proximal and a distal end, the drive member being rotatably disposed within and along a longitudinal axis of the guidewire shaft;
 an actuator connected to the proximal end of the drive member, the actuator imparting a rotation to the drive member;
 an asymmetrical rotating tip attached to the distal end of the drive member and driven in rotation about the longitudinal axis of the guidewire shaft by the drive member, the asymmetrical rotating tip including a protruding portion that projects from a plane defined by an outer surface of the guidewire shaft to render the rotating tip asymmetrical with respect to the longitudinal axis of the shaft. In this manner, the protruding portion creates a volume of revolution as the asymmetrical tip rotates, which facilitates crossing a vascular occlusion.

The asymmetrical rotating tip may includes an ultrasonic transducer or an optical fiber device mounted therein, to thereby obtain guidance information as the guidewire advances through the patient's vasculature. The drive member may be a drive shaft having a lumen therethrough to accommodate electrical leads connected to the ultrasonic transducer or the optical fiber, connected to an imaging device near the proximal end of the guidewire shaft. The ultrasonic transducer may be recessed within a well disposed within the asymmetrical rotating tip. The protruding portion of the asymmetrical rotating tip may project from the outer surface of the guidewire shaft by a distance selected within a range of 0.002 inches to 0.010 inches. The actuator may be a motorized actuator, a manual actuator, or a combination of these. The guidewire shaft may include a coiled wire and a polymeric tube in intimate contact with an outer diameter of the coil. In this manner, the tube in intimate contact with the coil prevents the coiled wire from buckling in or out when the guidewire is pushed through the patient's vasculature, thereby increasing the pushability and the column strength of the guidewire without substantially reducing its flexibility. The tube may be formed of, for example, polyimide or heat shrinkable TEFLON. A coupling member may be disposed between the distal end of the guidewire shaft and the asymmetrical rotating tip, the coupling member being bonded to the distal end of the shaft by an adhesive.

According to another exemplary embodiment of the present invention, a guidewire for crossing a vascular occlusion, comprises:

a guidewire shaft having a proximal end and a distal end;

a rotating drive member having a proximal and a distal end;

a coupling member attached to a distal end of the shaft, and having a through opening aligned with a longitudinal axis of the guidewire shaft to allow the drive member to rotate and slide therein, the coupling member including a distal angled surface oriented at predetermined acute angle relative to a plane perpendicular to the longitudinal axis of the guidewire shaft; and an asymmetrical tip attached to the distal end of the drive member and driven in rotation about the longitudinal axis of the guidewire shaft by the drive member, the asymmetrical tip including a proximal angled surface that, in one orientation, is parallel to and in intimate contact with the distal angled surface of the coupling member. In this manner, rotation of the asymmetrical tip against the distal angled surface of the coupling member causes the asymmetrical tip to reciprocate along the axis of the guidewire shaft over a distance determined at least by the predetermined angle, to thereby facilitate a crossing of a vascular occlusion by submitting the occlusion to both rotational and reciprocating movement of the asymmetrical tip.

A spring may be disposed near the proximal end of the drive member to bias the drive member in a proximal direction by a substantially constant force. The predetermined acute angle may be an angle selected within the range of about 2° to about 45°. The distal angled surface may be non-planar and may include one or more topographical features, and the proximal angled surface may be a mating non-planar surface including at least one corresponding topographical feature.

According to another preferred embodiment of the present invention, a catheter for treating vascular occlusions, comprises:

a catheter shaft having a proximal end and a distal end;

a rotating drive shaft member having a proximal and a distal end, the drive shaft member being disposed within and along a longitudinal axis of the shaft;

a guidewire disposed within the rotating drive shaft member;

a coupling member attached to a distal end of the catheter shaft, and having a through opening aligned with a longitudinal axis of the shaft to allow the drive shaft member to rotate and slide therein, the coupling member including a distal angled surface oriented at predetermined acute angle relative to a plane perpendicular to the longitudinal axis of the shaft; and an asymmetrical tip attached to the distal end of the drive shaft member and driven in rotation about the longitudinal axis of the shaft by the drive member, the asymmetrical rotating tip including a proximal angled surface that, in one orientation, is parallel to and in intimate contact with the distal angled surface of the coupling member, the asymmetrical rotating tip including an axial through bore for receiving the guidewire. In use, the guidewire is advanced near an occlusion site, whereupon the catheter is tracked over the guidewire to the occlusion site and the guidewire retracted within the catheter shaft. Rotation of the asymmetrical tip against the distal angled surface of the coupling member causes the asymmetrical tip to reciprocate and to displace and exert pressure on the occlusion, to thereby create a dissection plane along which the catheter may further advance.

The predetermined acute angle may be selected within the range of about 2° to about 45°. Alternatively, the predetermined acute angle may be substantially 0°. The asymmetrical tip may include a transducer or an optical fiber device mounted therein, to thereby obtain guidance information as the catheter advances through the patient's vasculature. The drive shaft member may be a drive shaft having a lumen therethrough to accommodate electrical leads connected to the transducer or the optical fiber, connected to an imaging device near the proximal end of the catheter shaft. The transducer may be recessed within a well disposed within the asymmetrical rotating tip. The asymmetrical tip may include a protrusion smoothly projecting in a radial direction relative to the longitudinal axis of the catheter shaft, the protuberance breaking a plane defined by an outer diameter of the catheter shaft. In this manner, the protruding portion creates a cylindrical volume of revolution as the asymmetrical tip rotates and reciprocates.

According to a still finther embodiment of the present invention, an instrument for crossing a vascular occlusion, comprises:

a shaft having a proximal end and a distal end;

a rotating drive member having a proximal and a distal end;

a coupling member attached to a distal end of the shaft, and having a through opening aligned with a longitudinal axis of the shaft to allow the drive member to rotate and slide therein, the coupling member including a distal angled surface, the distal angled surface being oriented at predetermined angle relative to a plane perpendicular to the longitudinal axis of the shaft, and a symmetrical tip attached to the distal end of the drive member and driven in rotation about the longitudinal axis of the shaft by the drive member, the symmetrical tip including a proximal angled surface that, in one orientation, is parallel to and in intimate contact with the distal angled surface of the coupling member. In this manner, rotation of the symmetrical tip against the distal angled surface of the coupling member causes the symmetrical tip to reciprocate along the axis of the shaft, to thereby facilitate a crossing of a vascular occlusion by submitting the occlusion to both rotational and reciprocating movement of the symmetrical tip.

The distal angled surface of the coupling member and the proximal angled surface of the symmetrical tip may be substantially planar. Alternatively, the distal angled surface of the coupling member and the proximal angled surface of the symmetrical tip may be substantially non-planar and may include mating topographical features. The distal angled surface of the coupling member and the proximal angled surface of the symmetrical tip may also be substantially non-planar and may include mating topographical features, and the predetermined angle may be substantially 0°. Alternatively still, the distal angled surface of the coupling member and the proximal angled surface of the symmetrical tip may be substantially non-planar and may include mating topographical features, and the predetermined angle may be selected within a range of about 2° to about 45°.

BRIEF DESCRIPTION OF THE DRAWINGS

For a further understanding of the objects and advantages of the present invention reference should be made to the following detailed description, taken in conjunction with the accompanying figures, in which.

DESCRIPTION OF THE PREFERRED EMBODIMENTS

Figure 1A:
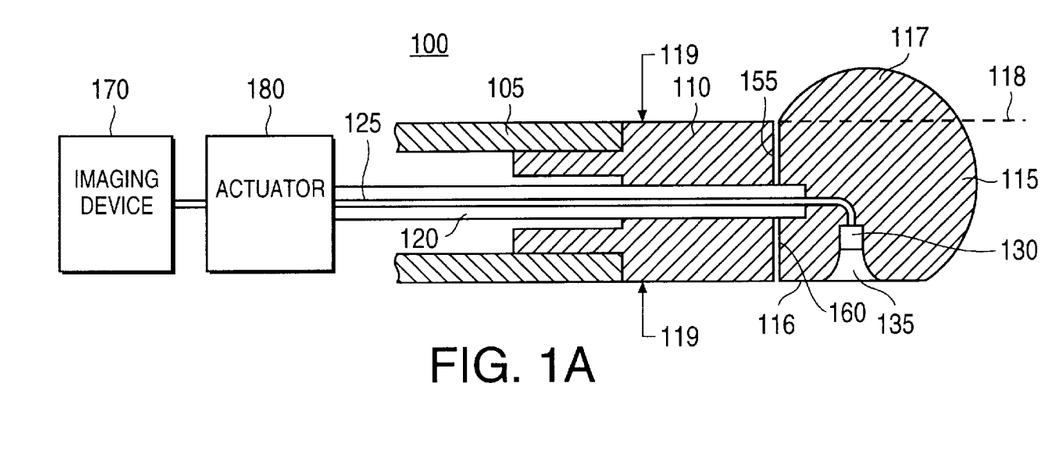
FIG. 1A is a cross sectional diagram of a guidewire having a rotating asymmetrical tip according to one embodiment of the present invention.
Figure 1B:
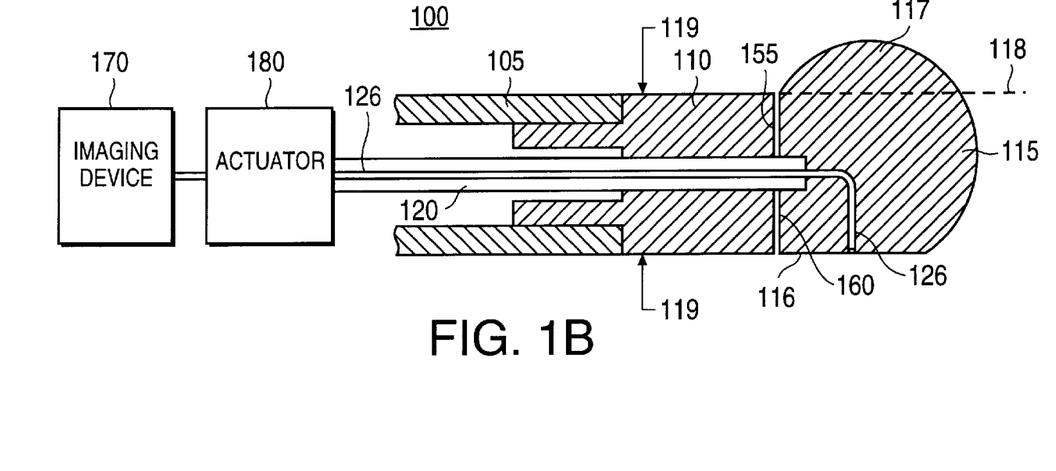
FIG. 1B is a cross sectional diagram of a guidewire having a rotating asymmetrical tip according to another embodiment of the present invention.
Figure 2:
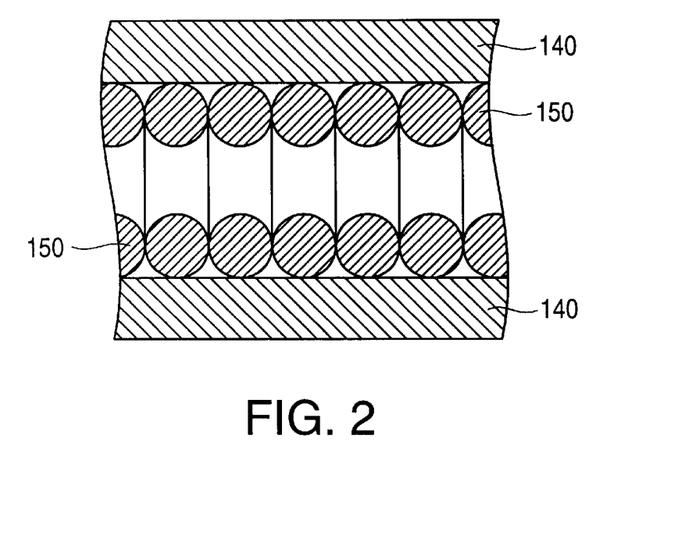
FIG. 2 is a cross sectional diagram of a detail of the guide wire shaft wall according to an embodiment of the present invention.

FIGS. 1A and 1B show cross-sections of guide wires with rotating asymmetrical tips according to the present invention. Reference numeral 105 is a guidewire shaft. To navigate the small diameter and tortuous regions of a patient's vasculature, the guidewire shaft 105 must be flexible. To achieve this goal, the guidewire shaft 105 according to the present invention, as shown in FIG. 2, may include a tightly coiled wire or ribbon 150. The coiled wire or ribbon 150 may be formed of stainlegs steel or a super-elastic metal such as NITINOL®. In one embodiment, the coiled wire or ribbon 150 is 0.002 inches in thickness.

In addition to a high degree of flexibility, the guidewire shaft 105 must exhibit good column strength, to enhance its ability to be pushed through small diameter lumens. To do this, the wire or ribbon coil 150 is surrounded by a thin walled polymeric tube 140 in intimate contact therewith. The thin walled tube 140 prevents the wire or ribbon coil 150 from buckling inward or outward when the guidewire shaft 105 is pushed through the patient's vasculature. Moreover, while the thin walled tube 140 increases the column strength of the guidewire shaft 105, it does not substantially decrease its flexibility. Therefore, the guidewire shaft 105 according to the present invention exhibits a high degree of flexibility as well as a good column strength, which increases its pushability and therefore improves the overall functionality of the device.

The thin walled tube 140 may be formed of polyimide having a thickness of approximately 0.0005 inches or greater. Alternatively, a heat shrinkable TEFLON® or PTFE tubing may be utilized, having a wall thickness of about 0.002. TEFLON® has the advantage that it is inherently slippery, which facilitates the guide wire's travels through tight and tortuous regions of the patient's vasculature. According to one embodiment of the present invention, the thin walled tube 140 is about 0.002 inches thick and the coiled wire or ribbon 150 is also 0.002 inches in thickness, for a total wall thickness of about 0.004 inches in thickness.

As shown in FIG. 1A and 1B, disposed within and along the longitudinal axis of the guidewire shaft 105 is a rotating drive wire 120. In one embodiment, the rotating drive wire 120 is about 0.005 inches and made of stainless steel. The proximal end of the drive wire 120 is attached to an actuator 180. The actuator 180 may either be a manual or motorized actuator, or a combination of the two. The actuator 180 rotates the drive wire 120 at a slow angular speed, within a range of about 2 to about 500 revolutions per minute. A manual actuator may be preferred for those interventions requiring precise manual control. In such a case, the actuator 180 may include a knob for manually rotating the drive wire 120, or for causing it to alternate between a forward and reverse direction, depending upon the desired therapeutic effect.

Near its distal end, the drive wire 120 runs through a coupling member 110. The coupling member 110 includes an opening aligned with the longitudinal axis of the guidewire shaft 105, allowing the drive wire 120 to rotate and to slide therethrough. The coupling member 110 is preferably made of a hard material. In one embodiment, this hard material is selected from a group consisting of 440, 304 or 316 stainless steel, titanium, titanium alloy or any hard material that provides a good hard bearing surface. The coupling member 110 is secured to the guidewire shaft 105 by means of an adhesive.

The distal surface 155 of the coupling member 110, in the embodiments illustrated in FIGS. 1A and 1B, is smooth and perpendicular to the longitudinal axis of the guidewire shaft 105, giving the coupling member 110—guidewire shaft 105 assembly a right cylindrical shape.

The distal end of the drive wire 120 is attached to an asymmetrical rotating tip 115. The asymmetrical rotating tip 115, according to the present invention, has an atraumatic distal end, which is relatively rounded and smooth. The asymmetrical tip 115 includes a protuberance 117, which projects smoothly therefrom, breaking a plane 118 defined by the outer diameter 119 of the guidewire shaft 105. This protuberance 117 may also simply be a convex portion of the tip 115 that locally projects further in the radial direction than the remainder of the tip 115. The asymmetrical tip 115 may also include a non-projecting portion 116, which is substantially co-planar with the plane 118 of the guidewire shaft 105. This co-planar non-projecting portion 116 of the asymmetrical tip 115 may be disposed generally radially opposite the protuberance 117. The asymmetrical tip 115 may also made of a hard material, and may be formed of the same material, as is the coupling member 110. In one embodiment of the present invention, the protuberance 117 projects from the plane 118 of the guidewire shaft a distance of about 0.002 to 0.010 inches.

In use, the guidewire 100 according to the present invention is introduced into the patient's vasculature, and advanced near the lesion or occlusion site. The drive shaft 120 rotates, under the action of either a manual or motorized actuator 180. As the drive shaft 120 is attached to the asymmetrical tip 115, the asymmetrical tip 115 rotates therewith. As the guide wire according to the present invention is small in size and very flexible, it is able to access a very small and tortuous lumen to reach the site of interest, where other, larger devices could not. One of the primary reasons for failure of common interventional procedures is the inability to cross a heavily stenosed region, where there is little or no channel left through and across the occlusion. By virtue of its flexibility and small size, the guidewire according to the present invention can be manipulated extremely close to such potentially life threatening occlusions. Once properly positioned at the site of interest, the asymmetrical tip 115 is rotated. As the protuberance 117 rotates, it sweeps a volume of revolution and displaces any mass it encounters in its path. As the lumen is quite narrow, the occlusive tissue is forced against the protuberance 117. In so doing, it may be flattened and/or compressed, in the case of soft or fatty deposits, under the combined pressure exerted by the protuberance 117 and the vessel walls. Alternatively, in the case of hard and calcified deposits such as plaque, the force exerted by the protuberance 117 of the asymmetrical tip 115 can break, displace and/or exert pressure on such deposits and create a dissection plane along which the guidewire 100 may further advance. In this manner, a channel through which body fluids such as blood may more freely pass may be created or widened. Alternatively still, the soft fatty deposits or the hard calcified deposits may be compressed and/or broken up to allow the guide wire according to the present invention to cross the occlusion site. Once across, a sheath may be slipped over the guidewire shaft and across the occlusion. Thereafter, the guide wire 100 may be retracted, removed from the patient's body, and exchanged for a standard guidewire over which another interventional tool may be tracked. Such interventional tool may be an atherectomy device, a balloon angioplasty device, a stent placement tool or the like. These devices may now be successfully be employed where they otherwise might not have been, as the occlusion has been crossed, and a channel therethrough created or sufficiently enlarged to allow their effective use.

According to another embodiment of the present invention, the asymmetrical and atraumatic tip 115 includes an imaging transducer 130, such as an ultrasonic transducer as shown in FIG. 1A or an optical fiber 126 as shown in FIG. 1B. As shown in FIG. 1A, an ultrasonic transducer 130 is disposed within the asymmetrical tip 115. This ultrasonic transducer 130 will create an image of the vessel walls and any occlusions thereof, to allow the guide wire 100 according to the present invention to stay within the desired boundaries and successfully negotiate the tortuous vessels in which the occlusion may be located. When an imaging transducer, whether ultrasonic or optical is present within the asymmetrical tip 115, reference numeral 120 designates a hollow drive shaft, as opposed to a solid drive wire. This allows electrical leads 125, in the case of the ultrasonic transducer 130 shown in FIG. 1A, or an optical fiber 126, as shown in FIG. 1B, to be disposed within the lumen of the drive shaft 120. When an ultrasonic transducer 130 is utilized, the transducer should be recessed from the surface of the asymmetrical tip 115. For this purpose, a well 135 is formed within the asymmetrical tip 115. This prevents the ultrasonic transducer 130 from generating too much energy too close to the target tissue, to prevent the phenomenon known as "ring down". The electrical leads 125 are then connected to an imaging device 170, to display an image of the tissue toward which the energy is directed. Alternatively, an optical transducer may be used, and embedded within the asymmetrical tip 115. An optical fiber 126 would then be disposed within the drive shaft 120 and connected, at its proximal end, to an optical imaging device 170. The resultant image may then be processed, using a variety of known techniques, such as OCT, or Optical Coherence Tomography. Examples of such processing are given in U.S. Pat. No. 5,321,501 issued on Jun. 14, 1994 to Swanson et al. and U.S. Pat. No. 5,459,570 issued Oct. 17, 1995 to Swanson et al., the disclosures of which are incorporated herewith in their entirety.

Of course, the guidewire 100 according to the present invention need not incorporate a transducer within the asymmetrical tip 115, to be therapeutically effective. Thus, the present invention is not to be limited to those embodiments wherein an imaging device is present within the asymmetrical tip 115.

Figure 3A:
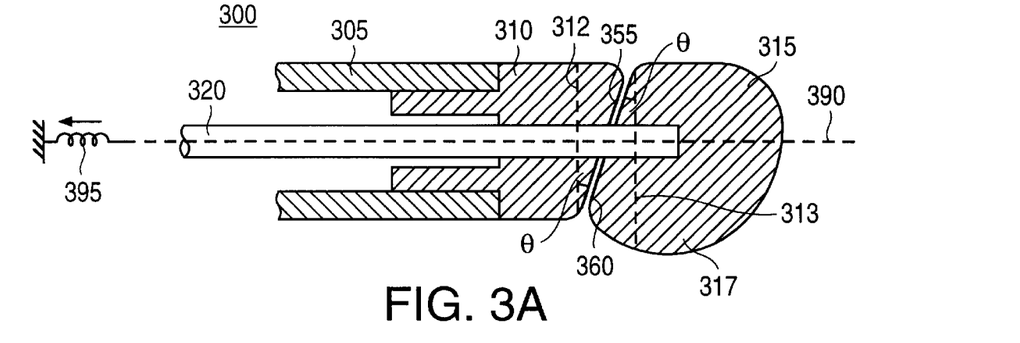
FIG. 3A is a cross sectional diagram of a guide wire having a rotating and reciprocating asymmetrical tip according to another embodiment of the present invention, wherein the asymmetrical tip is in a first orientation.
Figure 3B:
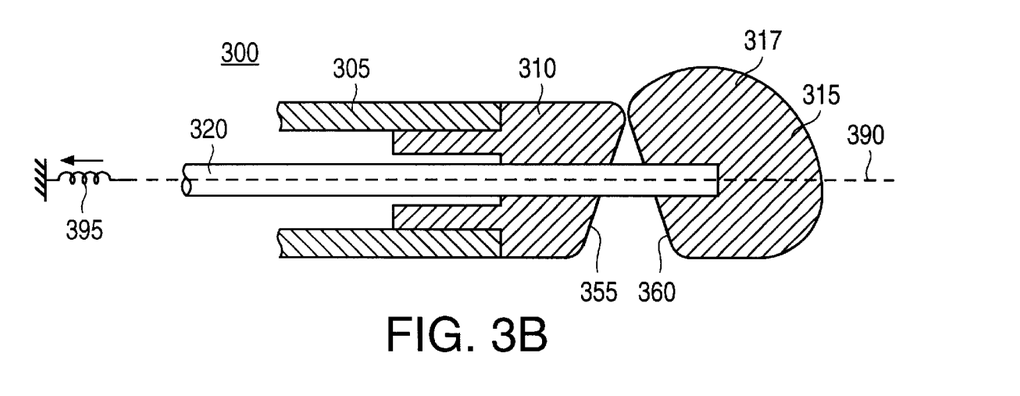
FIG. 3B is a cross sectional diagram of a guide wire having a rotating and reciprocating asymmetrical tip according to another embodiment of the present invention, wherein the asymmetrical tip is in a second orientation.

FIG. 3A and FIG. 3B show another embodiment of the present invention. FIGS. 3A and 3B show a guide wire 300 that is similar to the guidewire 100 of FIG. 1, but for the coupling member and the asymmetrical tip. The description of the guidewire 100 of FIGS. 1 and 2, with the exception of the description of the coupling member 110 and the asymmetrical tip 115, therefore, is incorporated herewith by reference.

The embodiment of the guidewire 300 of FIGS. 3A and 3B includes a coupling member 310, as well as a correspondingly shaped asymmetrical tip 315. The coupling member 310 includes a distal angled surface 355 oriented at a predetermined acute angle theta relative to a plane 312 that is perpendicular to the longitudinal axis 390 of the catheter shaft 305. This angle theta may be selected within the range of 2° to 45°. Therefore, unlike the embodiment of the guidewire 100 shown in FIG. 1, the guidewire 300 according to the present invention shown in FIGS. 3A and 3B includes a coupling member 310 having an angled distal surface 355. The asymmetrical tip 315 includes a correspondingly angled proximal surface 360. The proximal angled surface 360 of the asymmetrical tip 315 is angled at the same predetermined angled theta, as measured relative to a plane 313 that is perpendicular to the longitudinal axis 390 of the catheter shaft, as is the distal angled surface 355 of the coupling member 310. The tip 315 may be symmetrical. Alternatively, the tip 315 may be asymmetrical and may include a protuberance 317 or convex portion that is similar to the protuberance 117 illustrated in FIG. 1 and described in detail above. This detailed description, therefore, is incorporated herewith in its entirety. In the orientation of the asymmetrical tip 315 relative to the coupling member 310 shown in FIG. 3A, the angled proximal surface 360 is parallel to and in intimate contact with the distal angled surface 355 of the coupling member 310. In the orientation of the asymmetrical tip 315 shown in FIG. 3A, the angled proximal surface 360 is in full bearing contact with the angled distal surface 355 of the coupling member 310.

As the shaft rotates under the action of the actuator 180 (shown in FIGS. 1A and 1B), the asymmetrical tip 315 of the guide wire 300 of FIG. 3A rotates also. As the asymmetrical tip 315 rotates, the two angled surfaces 355, 360 bear against one another. As the drive wire or drive shaft 320 is mounted within the catheter shaft 305 so as to allow both rotation about and translation along the longitudinal axis 390 of the catheter shaft, the asymmetrical tip 315 attached thereto follows a reciprocating motion as it bears against the angled distal surface 355 of the coupling member 310.

FIG. 3B also shows the guidewire 300, the asymmetrical tip 315 having rotated approximately 180° away from the position shown in FIG. 3A Due to the co-action of the two angled surfaces 360 and 355 bearing against one another, the asymmetrical tip 315 shown in FIG. 3B is located at its maximum longitudinal displacement relative to the coupling member 310. This longitudinal displacement of the asymmetrical tip 315 is made possible by the angled surfaces 355, 360 as well as by the ability of the drive shaft or drive wire 305 to slide along the longitudinal axis 390 of the guidewire shaft 305. The longitudinal displacement of the asymmetrical tip 315 relative to the distal most portion of the coupling member 310 is determined by the angle theta of both the asymmetrical tip 315 and the coupling member 310. For example, if the outside diameter of a guidewire shaft is 0.0225 inches and a longitudinal displacement of 0.010 inches is desired, the tangent of the angle theta must be 0.010/0.0225 or 0.4444, making the angle theta equal to approximately 240. Other displacements may be chosen, by appropriately matching the angle theta to the outside diameter of the guidewire shaft 305 or the coupling member 310.

As the asymmetrical tip 315 shown in FIG. 3B is further driven in rotation about the longitudinal axis of the guidewire shaft, i.e., completing its revolution from the 180° position to the 360° position, it will return to the orientation shown in FIG. 3A. Therefore, as the asymmetrical tip 315 rotates, it will describe a reciprocating motion from the position shown in FIG. 3A to the position shown in FIG. 3B, and back.

To insure the return of the asymmetrical tip 315 from the position shown in FIG. 3B to the position shown in FIG. 3A, the rotating drive shaft or drive wire 305 may be biased by a substantially constant force directed in the proximal direction. This substantially constant force may be supplied by a spring 395 attached at or near the proximal end of the drive wire or shaft 320.

In use, the guidewire 300 is advanced near an occlusion site within the patient's vasculature. The rotation of the asymmetrical tip 315 against the distal angled surface 355 of the coupling member 310 then causes the asymmetrical tip 315 to reciprocate along the axis of the shaft 305 over a distance determined by the angle theta, as described above. The crossing of the vascular occlusion is thereby facilitated, as the occlusion is submitted to both rotational and reciprocating movement of the asymmetrical tip 315. Within the tight confines of the vessel walls and the constriction caused by the stenotic material at the occlusion site, this rotational and reciprocating motion exerts pressure on the occlusion over a cylindrical volume of space. Specifically, the protuberance 317 projecting from the plane defined by the outside diameter of the guidewire shaft 305 exerts radially directed pressure and displaces and/or breaks up a volume of stenotic material equal to its own volume. In this manner, a channel may be formed through the occlusion, or an existing channel widened. Thereafter, as with the first embodiment of the present invention, a sheath (not shown) may be slid over the guide wire 300, the guide wire 300 retracted and exchanged for a standard guidewire. A new interventional tool may then be tracked over this standard guidewire and placed into position across the occlusion to, for example, place a stent, perform an angioplasty or atherectomy procedure, or the like. The present invention, therefore, is especially useful where there is a total or near total chronic blockage of a blood vessel or any biological vessel, where this blockage or occlusion does not allow conventional instruments to cross or to reach the site of interest. After the guidewire 300 according to the present invention is employed, the stenotic material may be sufficiently compressed, displaced and/or broken up to allow the use of the aforementioned interventional tools to be utilized with a high degree of success.

It is to be noted that the guidewire of FIGS. 3A and 3B may be provided with either an ultrasonic transducer 130 or an optical transducer 126, in the same manner as described relative to FIGS. 1A and 1B. The description of such transducers and the means of connecting them to the proximal imaging device 170, therefore, is incorporated herewith in its entirety, as if repeated here in full.

Figure 4A:
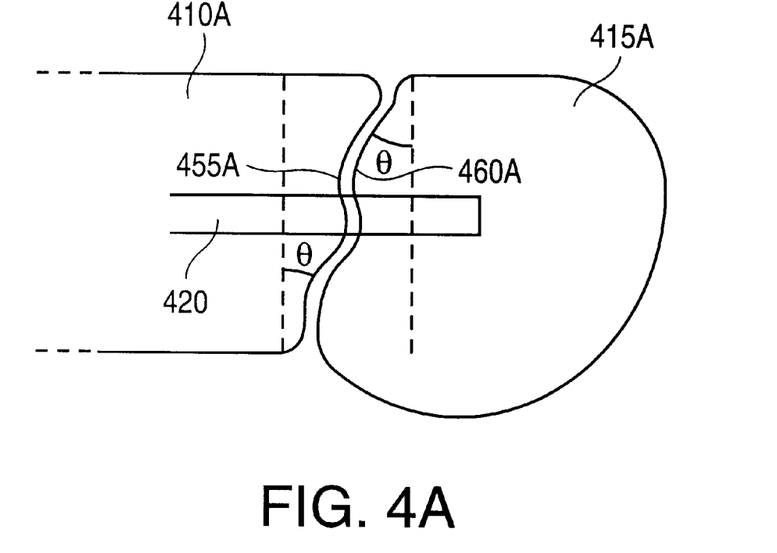
FIG. 4A is a cross sectional detailed view of another embodiment of a coupling member and of a corresponding asymmetrical tip, according to the present invention.
Figure 4B:
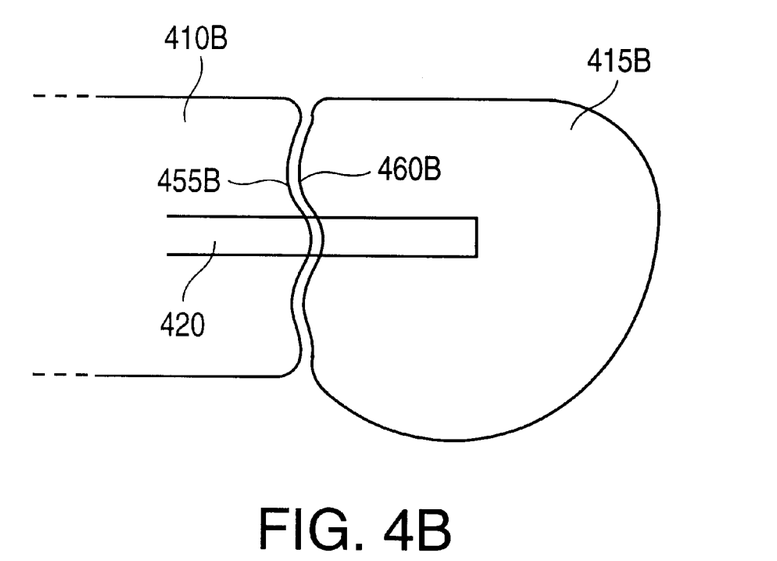
FIG. 4B is a cross sectional detailed view of another embodiment of a coupling member and of a corresponding asymmetrical tip, according to the present invention.

Other configurations of the coupling member and tip may be employed. For example, as show in FIG. 4A, the angled distal surface 455A of the coupling member 410 or, as shown in FIG. 4B, the distal surface 455B of the coupling member 410 may be non-planar and include a number of topographical features such as ridges, peaks and valleys, bumps, depressions or other similar features, which alter the motion of the asymmetrical tip 415 as the asymmetrical tip 415 is driven by the drive wire or shaft 420. In FIG. 4A, the angle theta has a non-zero value, while it is zero in FIG. 4B. The proximal surface 460A, 460B of the asymmetrical tip 415, in FIGS. 4A and 4B, respectively, would then also be non-planar and be provided with corresponding topographical features to insure a mating relationship with distal surfaces 455A, 455B, respectively.

Figure 6A:
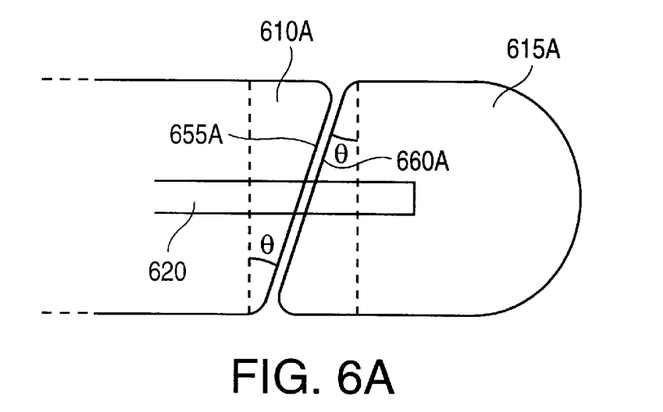
FIG. 6A is a cross sectional detailed view of another embodiment of the present invention, showing a coupling member and a corresponding symmetrical tip.
Figure 6B:
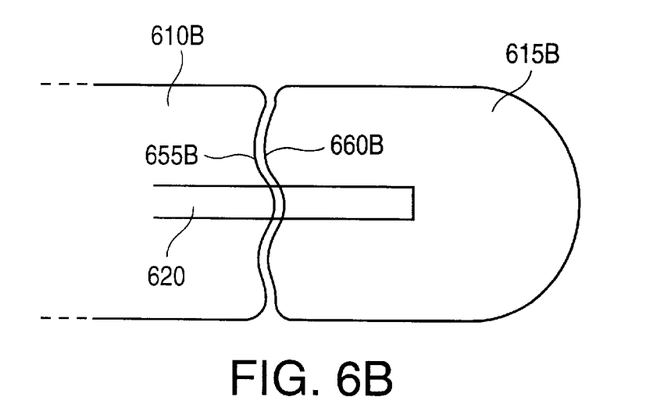
FIG. 6B is a cross sectional detailed view of yet another embodiment of the present invention, showing a coupling member and a corresponding symmetrical tip.
Figure 6C:
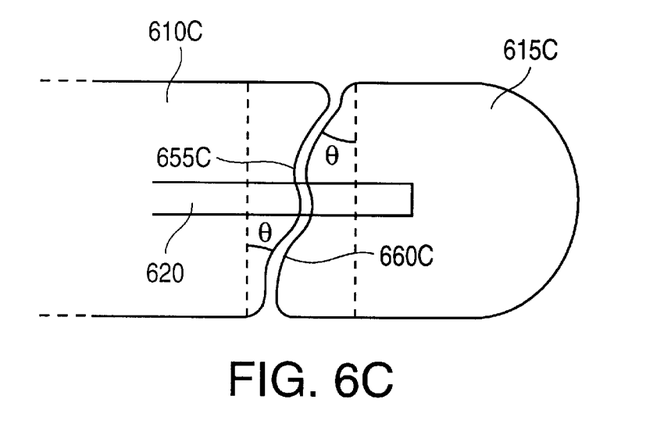
FIG. 6C is a cross sectional detailed view of a further embodiment of the present invention, showing a coupling member and a corresponding symmetrical tip.

Alternatively, as shown in FIGS. 6A through 6C, the tip of the guidewires or the catheters according to the present invention may be symmetrical about the longitudinal axis of the guidewire or catheter shaft. For example, as shown in FIGS. 6A and 6C, the angled distal surfaces 655A, 655C of the coupling member 610A, 610C may be planar (FIG. 6A) or non-planar (FIG. 6C) and include a number of topographical features such as ridges, peaks and valleys, bumps, depressions or other similar features, which alter the motion of the symmetrical tip 615A, 615C as the symmetrical and atraumatic tip 615A, 615C is driven by the drive wire or drive shaft 620. The proximal surface 660A, 660C of the symmetrical tip 615A, 615C in FIGS. 6A and 6C, respectively, would then also be non-planar and be provided with corresponding topographical features to insure a mating relationship with distal surfaces 655A, 655C, respectively. In FIGS. 6A and 6C, the angle theta has a non-zero value.

Alternatively still, as shown in FIG. 6B, the coupling member 610B could be provided with a distal surface 655B that is non-planar and that includes a number of topographical features such as ridges, peaks and valleys, bumps, depressions or other similar features, which alter the motion of the symmetrical and atraumatic tip 615B as the symmetrical tip 615B is driven by the drive wire or drive shaft 620. The proximal surface 660B of the symmetrical tip 615B in FIG. 6B would then also be non-planar and be provided with corresponding topographical features to insure a mating relationship with distal surfaces 655B. In contrast to FIGS. 6A and 6C, the angle theta in FIG. 6B has a substantially zero value.

The coupling member-tip configurations shown in FIGS. 4a, 4B, 6A, 6B and 6C are readily applicable to both the guide wire and catheter configurations shown in FIGS. 1A, 1B, 3A and 3B and FIG. 5.

For example, the asymmetrical tip 115 of FIG. 1 could be caused to undergo a certain measure of reciprocal motion by providing the distal surface 155 of the coupling member 115 with a number of smooth peaks and valleys or bumps and depressions, and by providing the proximal surface 160 of the asymmetrical tip 115 with corresponding and mating features. Such features may also be employed in the embodiment of the guidewire according to the present invention shown in FIGS. 3A and 3B.

In this manner, for example, another motion of different amplitude may be superimposed upon the reciprocating motion of the asymmetrical tip 415 caused by the angled surfaces 455A, 460B, by providing the respective surfaces with topographical features, such as bumps and depressions or a series of ridges.

Figure 5:
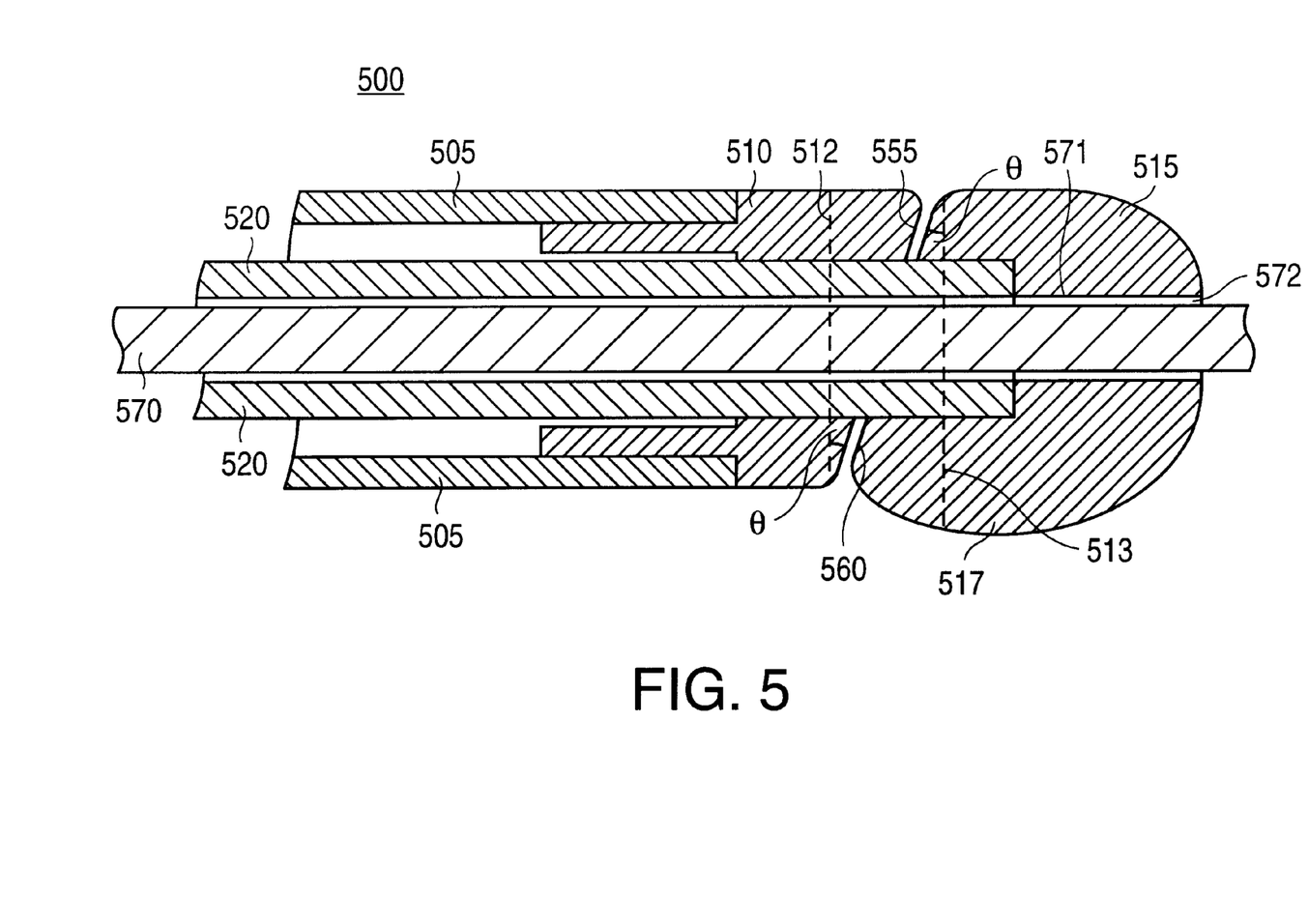
FIG. 5 is a cross sectional diagram of a catheter according to another embodiment of the present invention.

FIG. 5 shows another embodiment of the present invention. FIG. 5 illustrates a catheter 500 with a rotating and reciprocating asymmetrical tip 515. The catheter 500 includes a catheter shaft 505. The catheter shaft 505, in one embodiment, has an outer diameter of 0.050 inches. Disposed along the longitudinal axis of and within the catheter shaft 505, is a rotating drive shaft 520 formed of, for example, stainless steel, a titanium alloy, or the like. In one embodiment, the rotating drive shaft 520 has an outer diameter of 0.040 inches. The proximal end of the drive shaft 520, as shown in FIG. 1, is connected to an actuator 180, which may be manual, motorized or a combination thereof The distal end of the rotating drive shaft 520 is embedded within the asymmetrical tip 515, to cause the tip 515 to rotate along with the drive shaft 520. Disposed within the lumen of the drive shaft 520 is a guidewire 570 made of; for example, a super elastic metal such as NITINOL ®, stainless steel or some other suitable material. In one embodiment of the catheter 500 according to the present invention, the guidewire 570 has an outer diameter of 0.014 inches.

A coupling member 510 is attached to the distal end of the catheter shaft 505. The coupling member 510 includes a through opening aligned with the longitudinal axis of the catheter shaft 505 to allow the drive shaft 520 to rotate and to slide therethrough. The coupling member 510 further includes a distal angled surface 555 oriented at predetermined acute angle theta relative to a plane 512 that is perpendicular to the longitudinal axis of the catheter shaft 505.

An asymmetrical and atraumatic rounded tip 515 is attached to the distal end of the rotating drive shaft 520, and is driven in rotation about the longitudinal axis of the catheter shaft 505. The asymmetrical rotating tip 515 includes a proximal angled surface 560 that, in one orientation, is parallel to and in intimate contact with the distal angled surface 555 of the coupling member 510. The proximal surface 560 is also inclined relative to a plane 513 that is perpendicular to the longitudinal axis of the catheter shaft, at the same angle theta as the distal angled surface 555 of the coupling member 510. The asymmetrical rotating tip 515 also includes an axial through bore 571 for receiving the guidewire 570, the guidewire 570 emerging from the asymmetrical tip 515 at the distal most portion 572 thereof The angle theta may be selected within a range of about 2° to about 45°. In one embodiment, the distance over which the asymmetrical tip travels is on the order of 0.015 inches. As the outer diameter of the catheter shaft 505, in one embodiment is 0.050 inches, it follows that the angle theta, which will achieve this reciprocating travel distance, is about 17°.

The asymmetrical tip 515 of the catheter 500 may also include ultrasonic or optical transducers embedded therein, in the same manner as was described relative to the inventions shown in FIGS. 1A through 3B. The descriptions thereof are, therefore, incorporated herewith.

To insure that the asymmetrical tip 515 returns to its proximal most position illustrated in FIG. 5 after having rotated 180°, the rotating drive shaft 520 may biased by a substantially constant force directed in the proximal direction. A spring 395, as shown in FIG. 3A and 3B may, therefore, be attached to the drive shaft 520 near its proximal end, which spring 395 will bias the asymmetrical tip 515 in the proximal direction and insure that the reciprocating movement of the tip 515 is sustained.

In use, the guidewire 570 is advanced near an occlusion site, whereupon the catheter 500 is tracked over the guidewire 570 to the occlusion site. The distal end of the guidewire 570 is then retracted within the catheter shaft 505. The rotation of the proximal surface 560 of the asymmetrical tip 515 against the distal angled surface 555 of the coupling member 510 then causes the asymmetrical tip 515 to reciprocate, thus displacing and exerting pressure on the occlusion. This creates a dissection plane along which the catheter may further advance. The force exerted by the rotation and reciprocal motion of the asymmetrical tip 515 upon the stenotic tissue may compress or break up the occlusion. An existing channel through the occlusion may be enlarged or a totally occluded vessel may be provided with a new channel through which the guidewire 570 may be further advanced. This guidewire 570, thereafter, may be left in place within the patient's vasculature, and the catheter 500 removed and exchanged for another interventional tool, which may be tracked over the guidewire 570 to the lesioned or occluded site for further procedures.

The non-planar surfaces 455A, 460A described relative to FIG. 4A may be substituted for the distal angled surface 555 of the coupling member 510 and the proximal angled surface 560 of the asymmetrical and atraumatic tip 515 of the catheter 500, respectively. These descriptions, therefore, are omitted to avoid unnecessary repetition and are incorporated herewith in their entirety.

While the foregoing detailed description has described preferred embodiments of the present invention, it is to be understood that the above description is illustrative only and not limiting of the disclosed invention. For example, the various elements of the guide wires and the catheter may be formed of materials other than those specifically enumerated without, however, departing from the scope and spirit of the present invention. Moreover, the angle theta for both the distal surface of the coupling member and the proximal surface of the asymmetrical tip may be zero. In such a case, to achieve the reciprocal motion described above, the above-cited surfaces may include a number of topographical features. Further modifications will occur to those of skill in this art, and all such modifications are deemed to fall within the scope of the present invention. Thus, the invention is to be limited only by the claims as set forth below.

What is claimed is:

1. A guidewire for crossing vascular occlusions comprising:
   a guidewire shaft having a proximal end and a distal end, the distal end being perpendicular to an outer surface of the guidewire shaft such that the outer surface of the guidewire shaft and the distal end define a right cylinder;
   a drive member having a proximal and a distal end, the drive member being rotatably disposed within and along a longitudinal axis of the guidewire shaft;
   an actuator connected to the proximal end of the drive member, the actuator capable of imparting rotational movement to the drive member, and
   an asymmetrical and atraumatic rotating tip attached to the distal end of the drive member, the asymmetrical and atraumatic rotating tip comprising,
      a planar proximal end and a rounded distal end, wherein the planar proximal end is substantially parallel to and in very close proximity to the distal end of the guidewire shaft;
      a smooth, rounded outer surface comprising,
         a portion that substantially conforms to the right cylinder defined by the guidewire shaft; and a protruding portion that locally projects radially from the longitudinal axis of the guidewire shaft beyond the right cylinder; and at least one image transducer mounted in the asymmetrical and atraumatic tip for obtaining guidance information as the guidewire advances through a patient's vasculature, wherein the at least one image transducer is mounted in a recess in the portion of the atraumatic rotating tip that substantially conforms to the right cylinder defined by the guidewire shaft.

2. A guidewire for crossing vascular occlusions, comprising:

a guidewire shaft having a proximal end and a distal end, the distal end being perpendicular to an outer surface of the guidewire shaft such that the outer surface of the guidewire shaft and the distal end define a right cylinder;

a drive member having a proximal and a distal end, the drive member being rotatably disposed within and along a longitudinal axis of the guidewire shaft, rein the drive member is a shaft having a lumen therethrough to accommodate at least one electrical lead coupled to an imaging device near the proximal end of the guidewire shaft;

an actuator connected to the proximal end of the drive member, the actuator capable of imparting rotational movement to the drive member, and an asymmetrical and atraumatic rotating tip attached to the distal end of the drive member, the asymmetrical and atraumatic rotating tip comprising, a planar proximal end and a rounded distal end, wherein the planar proximal end is substantially parallel to and in very close proximity to the distal end of the guidewire shaft;

a smooth, rounded outer surface comprising, a portion that substantially conforms to the right cylinder defined by the guidewire shaft; and a protruding portion that locally projects radially from the longitudinal axis of the guidewire shaft beyond the right cylinder; and at least one image transducer mounted in the asymmetrical and atraumatic tip for obtaining guidance information as the guidewire advances trough a patient's vasculature, wherein the at least one image transducer is mounted in a recess in the portion of the atraumatic rotating tip that substantially conforms to the right cylinder defined by the guidewire shaft, and wherein the at least one image transducer is coupled to the at least one electrical lead.

3. An instrument comprising:

a shaft having a proximal end and a distal end, the distal end being perpendicular to an outer surface of the shaft such that the outer surface of shaft and the distal end define a right cylinder;

an asymmetrical and atraumatic tip adjacent to the distal end of the shaft for crossing a vascular occlusion, wherein the asymmetrical and atraumatic tip comprises, a rounded and smooth distal end;

a planar proximal end; and a circumference between the rounded and smooth distal end and the planar proximal end, comprising, a portion that substantially conforms to the right cylinder; and a protruding portion that protrudes radially from a longitudinal axis of the shaft beyond the right cylinder; and at least one of an ultrasonic transducer and an optical fiber device for obtaining guidance information as the instrument advances through a patient's vasculature, wherein the at least one of an ultrasonic transducer and an optical fiber is positioned in the portion that substantially conforms to the right cylinder;

a drive member having a proximal and a distal end, the asymmetrical and atraumatic tip being attached to the distal end of the drive member such that the planar proximal end of the asymmetrical and atraumatic tip is in close proximity to and substantially parallel to the distal end of the shaft; and an actuator coupled to the proximal end of the drive member, wherein the actuator actuates the drive member to cause a rotational movement of the asymmetrical and atraumatic tip relative to the longitudinal axis of the shaft.

4. An instrument for crossing a vascular occlusion, comprising:

a shaft having a proximal end and a distal end, the distal end being perpendicular to an outer surface of the shaft such that the outer surface of shaft and the distal end define a right cylinder;

an asymmetrical and atraumatic tip adjacent to the distal end of the shaft for crossing a vascular occlusion, wherein the asymmetrical and atraumatic tip comprises, a rounded and smooth distal end;

a planar proximal end; and a circumference between the rounded and smooth distal end and the planar proximal end, comprising, a portion that substantially conforms to the right cylinder; and a protruding portion that protrudes radially from a longitudinal axis of that shaft beyond the right cylinder; and at least one of an ultrasonic transducer and an optical fiber for obtaining guidance information as the instrument advances through a patient's vasculature, wherein the at least one of an ultrasonic transducer and an optical fiber is positioned in the portion that substantially conforms to the right cylinder;

a drive member having a proximal and a distal end, the asymmetrical and atraumatic tip being attached to the distal end of the drive member such that the planar proximal end of the asymmetrical and atraumatic tip is in close proximity to and substantially parallel to the distal end of the shaft the drive member including a lumen which houses electrical leads for the ultrasonic transducer, the electrical leads and the optical fiber being connected to an imaging device near the proximal end of the shaft; and an actuator coupled to the proximal end of the drive member, wherein the actuator actuates the drive member to cause a rotational movement of the asymmetrical and atraumatic tip relative to the longitudinal axis of the shaft.

5. A guidewire for crossing vascular occlusions, comprising:

a guidewire shaft having a proximal end and a distal end, the distal end being perpendicular to an outer surface of the guidewire shaft such that the outer surface of the guidewire shaft and the distal end define a right cylinder;

a drive member having a proximal and a distal end, the drive member being rotatably disposed within and along a longitudinal axis of the guidewire shaft;

an actuator connected to the proximal end of the drive member, the actuator capable of imparting rotational movement to the drive member, and an asymmetrical and atraumatic rotating tip attached to the distal end of the drive member, the asymmetrical and atraumatic rotating tip comprising,
- a planar proximal end and a rounded distal end, wherein the planar proximal end is substantially parallel to and in very close proximity to the distal end of the guidewire shaft;
- a smooth, rounded outer surface comprising,
  - a portion that substantially conforms to the right cylinder defined by the guidewire shaft; and
  - a protruding portion that locally projects radially from the longitudinal axis of the guidewire shaft beyond the right cylinder; and
- at least one image transducer comprising one of an ultrasonic transducer and an optical fiber device, the at least one image transducer mounted in the asymmetrical and atraumatic tip for obtaining guidance information as the guidewire advances through a patient's vasculature, wherein the at least one image transducer is mounted in a recess in the portion of the atraumatic rotating tip that substantially conforms to the right cylinder defined by the guidewire shaft.

* * * * *